United States Patent

Maurer et al.

[11] 4,335,134
[45] Jun. 15, 1982

[54] PESTICIDALLY ACTIVE N,N-DIMETHYL-CARBAMIC ACID O-(4,6-DIHYDRO-2H-THIENO[3,4-C]PYRAZOL-3-YL) ESTERS AND 5-OXIDES AND 5,5-DIOXIDES THEREOF

[75] Inventors: Fritz Maurer, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 225,548

[22] Filed: Jan. 15, 1981

[30] Foreign Application Priority Data

Jan. 29, 1980 [DE] Fed. Rep. of Germany ....... 3003019

[51] Int. Cl.³ .................... A01N 43/56; C07D 495/04
[52] U.S. Cl. ................................. 424/273 P; 548/370; 548/359
[58] Field of Search ..................... 548/370; 424/273 P

[56] References Cited

U.S. PATENT DOCUMENTS 3,649,641 3/1972 Kim et al. ........................... 548/370
4,042,373 8/1977 Moje ................................... 548/370

OTHER PUBLICATIONS

Bauer et al., J. Med. Chem., 1971, vol. 14 (5), pp. 454–456.

Primary Examiner—John M. Ford
Assistant Examiner—N. Harkaway
Attorney, Agent, or Firm—Sprung, Horn, Kramer & Woods

[57] ABSTRACT

Pesticidally active N,N-dimethyl-carbamic acid O-(2-substituted-4,6-dihydro-2H-thieno[3,4-c] pyrazol-3-yl esters or 5-oxides or 5,5-dioxides thereof of the formula

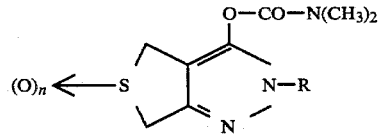

in which
R is an alkyl, alkenyl, alkynyl, cycloalkyl, aralkyl or aryl radical, and
n is 0, 1 or 2.

The hydroxypyrazoles corresponding to such esters are also novel.

8 Claims, No Drawings

PESTICIDALLY ACTIVE N,N-DIMETHYL-CARBAMIC ACID O-(4,6-DIHYDRO-2H-THIENO[3,4-C]PYRAZOL-3-YL) ESTERS AND 5-OXIDES AND 5,5-DIOXIDES THEREOF

The invention relates to certain new N,N-dimethyl-carbamic acid O-(4,6-dihydro-2H-thieno[3,4-c]pyrazol-3-yl) esters and 5-oxides and 5,5-dioxides thereof, to a process for their preparation and to their use as agents for combating pests, especially as insecticides.

It is known that certain N,N-dimethyl-carbamic acid O-pyrazolyl esters, for example N,N-dimethyl-carbamic acid O-(1-phenyl-3-methyl-pyrazol-5-yl) ester and O-(1-isopropyl-3-methyl-pyrazol-5-yl) ester, have insecticidal properties (see Swiss Patent Specification No. 282,655).

However, the insecticidal action of these known compounds is not always satisfactory, especially in the case of low concentrations of active compound and when small amounts are applied.

The present invention now provides: (1), as new compounds, the N,N-dimethyl-carbamic acid O-(4,6-dihydro-2H-thieno[3,4-c]pyrazol-3-yl) esters and 5-oxides and 5,5-dioxides thereof, of the general formula

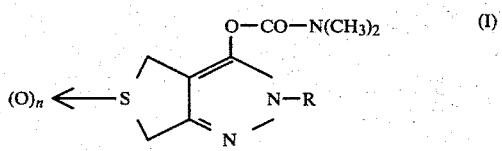

in which
R represents an optionally substituted alkyl, alkenyl, alkynyl, cycloalkyl, aralkyl or aryl radical and
n represents zero, 1 or 2,
and (2) a process for the preparation of a compound of the formula (I), in which
(α) a 4,6-dihydro-2H-thieno[3,4-c]-3-hydroxy-pyrazole or 5-oxide or 5,5-dioxide thereof, of the general formula

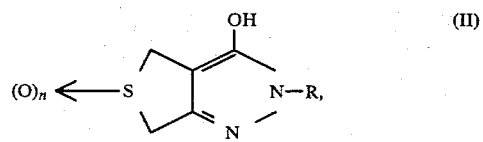

in which R and n have the meanings indicated above, is carbamoylated, or (β), provided a compound of the formula (I) in which n represents 1 or 2 is to be prepared, a compound of the formula (I) in which n represents zero is oxidized.

The invention also provides: (3), as new compounds, the 4,6-dihydro-2H-thieno[3,4-c]-3-hydroxy-pyrazoles and 5-oxides and 5,5-dioxides thereof, of the general formula

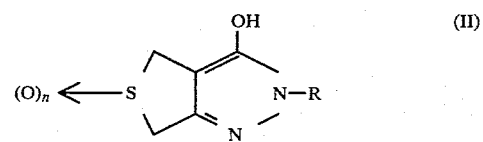

in which

R represents an optionally substituted alkyl, alkenyl, alkynyl, cycloalkyl, aralkyl or aryl radical and
n represents zero, 1 or 2,
and (4), a process for the preparation of a compound of the formula (II), in which a 4-oxo-tetrahydrothiophene-3-carboxylic acid ester of the general formula

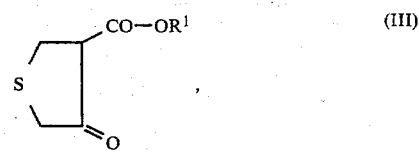

in which $R^1$ represents alkyl with 1 to 4 carbon atoms, is reacted with a hydrazine derivative of the general formula $$H_2N-NH-R \qquad (IV),$$

in which R has the meaning indicated above, if appropriate in the presence of an acid acceptor and if appropriate using a diluent, and, if required, the product is oxidized by any customary method.

The N,N-dimethyl-carbamic acid O-(4,6-dihydro-2H-thieno[3,4-c]pyrazol-3-yl) esters and 5-oxides and 5,5-dioxides thereof, of the formula (I) are distinguished by a high pesticidal activity, in particular a high insecticidal activity.

Surprisingly, the compounds of the formula (I) exhibit a considerably more powerful insecticidal action than the compounds of analogous structure and the same type of action which are known from the state of the art.

Preferred compounds of the formula (I) are those in which
R represents $C_1$–$C_5$-alkyl which is optionally substituted by cyano, or represents $C_3$–$C_6$-cycloalkyl and
n represents zero, 1 or 2.

The carbamoylation for the preparation of a compound of the formula (I) can be carried out by a procedure in which (2a) a 4,6-dihydro-2H-thieno[3,4-c]-3-hydroxy-pyrazole or 5-oxide or 5,5-dioxide thereof, of the general formula

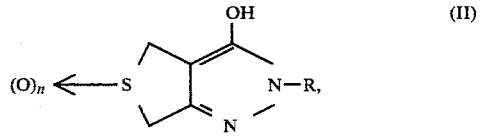

in which R and n have the meanings indicated above, is reacted with N,N-dimethylcarbamic acid chloride, if appropriate in the presence of an acid acceptor and if appropriate using a diluent, or (2b) a compound of the formula (II) above is reacted with phosgene and the product is then reacted with dimethylamine, if appropriate in the presence of an acid acceptor and if appropriate using a diluent.

The oxidation of a compound of the formula (I) in which n represents O to give a compound in which n represents 1 can be carried out by a procedure in which (2c) a compound of the formula (I) in which n represents zero is reacted with at least approximately the equimolar amount of hydrogen peroxide, if appropriate using a diluent.

The oxidation of a compound of the formula (I) in which n represents 0 to give a compound in which n represents 2 can be carried out by a procedure in which (2d) a compound of the formula (I) in which n represents zero is reacted with at least two molar equivalents of m-chloroperbenzoic acid, if appropriate in the presence of a diluent.

If, for example, 2-isobutyl-4,6-dihydro-2H-thieno[3,4-c]-3-hydroxy-pyrazole is used as the starting substance in process variants (2a) and (2b) and N,N-dimethyl-carbamic acid O-(2-propyl-4,6-dihydro-2H-thieno[3,4-c]-pyrazol-3-yl ester is used as the starting substance in process variants (2c) and (2d), the reactions of these starting substances can be outlined by the following equations:

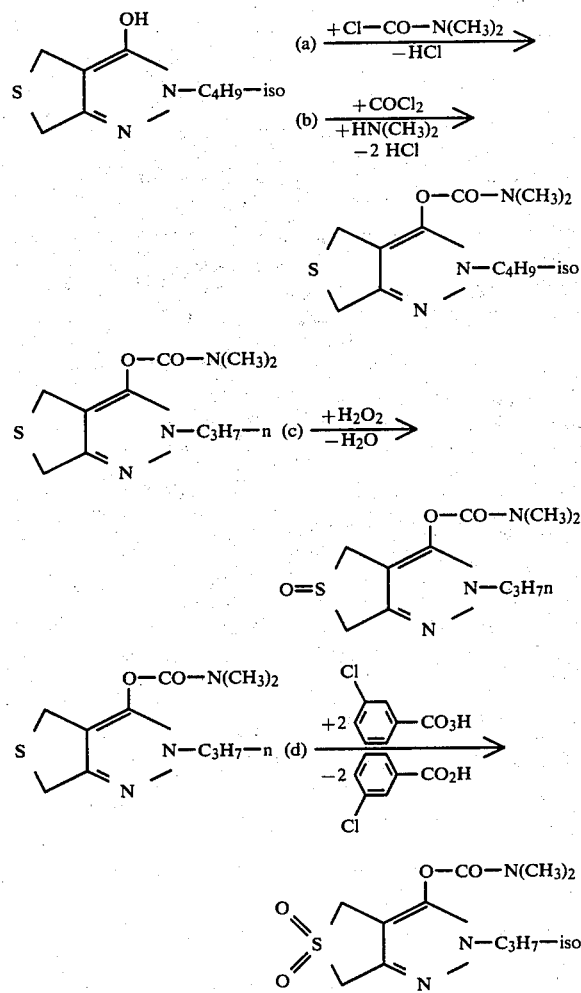

Formula (II) provides a definition of the 4,6-dihydro-2H-thieno[3,4-c]-3-hydroxy-pyrazoles, and 5-oxides and 5,5-dioxides thereof, to be used as starting substances in process variants (2a) and (2b). Preferably, in this formula, R represents $C_1$–$C_5$-alkyl, which is optionally substituted by cyano, or $C_3$–$C_6$-cycloalkyl and
n represents zero.

Examples of compounds of the formula (II) which may be mentioned are: 2-methyl-, 2-ethyl-, 2-n-propyl-, 2-iso-propyl-, 2-n-butyl-, 2-iso-butyl-, 2-sec.-butyl, 2-tert.-butyl-, 2-n-pentyl-, 2-iso-pentyl-, 2-sec.-pentyl-, 2-tert.-pentyl-, 2-(1-ethyl-propyl)-, 2-(2-cyano-ethyl)-, 2-cyclopropyl-, 2-cyclopentyl- and 2-cyclohexyl-4,6-dihydro-2H-thieno-[3,4-c]-3-hydroxy-pyrazole.

The compounds of the formula (II) have not hitherto been described in the literature. They are obtained as described above under (4), by a process in which compounds of the formula (III) above, for example 4-oxo-tetrahydro-thiophene-3-carboxylic acid methyl ester, are reacted with hydrazine derivatives of the formula (IV) above, in which R preferably represents $C_1$–$C_5$-alkyl which is optionally substituted by cyano, or $C_3$–$C_6$-cycloalkyl, if appropriate in the presence of an acid acceptor, for example sodium methylate, and if appropriate using a diluent, for example methanol, at temperatures between 10° and 100° C. For working up, the mixture is diluted with water, the organic solvent is distilled off, if appropriate, the solution which remains is rendered weakly acid and the product which has separated out as crystals is isolated by filtration.

Examples of the precursors of the formula (IV) which may be mentioned are: methyl-, ethyl-, n-propyl-, iso-propyl-, n-butyl-, iso-butyl-, sec.-butyl-, tert.-butyl-, n-pentyl-, iso-pentyl-, sec.-pentyl-, tert.-pentyl-, 1-ethyl-propyl-, 2-cyano-ethyl-, cyclopropyl-, cyclopentyl- and cyclohexyl-hydrazine.

The precursors of the formulae (III) and (IV) are known.

The formula (I) provides a definition of the N,N-dimethyl-carbamic acid O-(4,6-dihydro-2H-thieno[3,4-c]pyrazol-3-yl) esters to be used as starting substances in process variants (2c) and (2d), with the proviso that n represents zero.

Preferably, in this formula, R represents $C_1$–$C_5$-alkyl, which is optionally substituted by cyano, or $C_3$-$C_6$-cycloalkyl.

Process variants (2a) to (2d) are preferably carried out using a diluent. Possible diluents are virtually any of the inert organic solvents. These include, as preferences, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene; ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone; esters, such as methyl acetate and ethyl acetate; nitriles, for example acetonitrile and propionitrile; amides, for example dimethylformamide, dimethylacetamide and N-methylpyrrolidone; and dimethylsulphoxide, tetramethylene sulphone and hexamethylphosphoric acid triamide.

Process variant (2c) is advantageously carried out using an aliphatic carboxylic acid, for example formic acid, acetic acid or propionic acid, as a diluent.

Process variants (2a) and (2b) are in general carried out using an acid acceptor. Any of the customary acid-binding agents can be used as acid acceptors. Acid-binding agents which have proved particularly suitable are alkali metal carbonates, such as sodium carbonate and potassium carbonate, alkali metal alcoholates, such as sodium methylate or ethylate and potassium methylate or ethylate, and aliphatic, aromatic or heterocyclic amines, for example triethylamine, trimethylamine, dimethylaniline, dimethylbenzylamine and pyridine.

The process according to the invention is in general carried out at temperatures between 0° and 150° C. The temperature range between 20° and 100° C. is preferred for process variant (2a) and the range between 0° and 50° C. is preferred for process variants (2b), (2c) and (2d). The reactions are in general carried out under normal pressure.

For carrying out process variants (2a) or (2b), in general between 1.0 and 1.3, preferably between 1.0 and 1.15, mols of N,N-dimethylcarbamic acid chloride or phosgene and diethylamine are employed per mole of hydroxypyrazole of the formula (II). The reaction is in general carried out in a diluent in the presence of an acid acceptor. When the reaction has ended, the mixture is diluted with water and extracted with a water-immiscible organic solvent, for example toluene. The organic phase is dried and filtered and the solvent is distilled off from the filtrate under reduced pressure.

The reactants are preferably employed in equimolar amounts in process variant (2c). If diluents which are water-miscible are used, these are distilled off in vacuo when the reaction has ended. The residue is then dissolved in a water-immiscible solvent, for example methylene chloride, and worked up by customary methods, for example by washing, drying and filtering and distilling off the solvent from the filtrate.

The m-chloro-perbenzoic acid used as the oxidizing agent in process variant (2d) is usually employed in excess, and preferably between 2 and 3 mols are employed per mol of N,N-dimethyl-carbamic acid O-(2H-thieno-[3,4-c]-pyrazol-3-yl) ester. The reaction is in general carried out in a water-immiscible solvent. When the reaction has ended, the mixture is washed until neutral, dried and filtered and the solvent is distilled off from the filtrate in vacuo.

The new compounds are generally obtained in the form of oils, some of which cannot be distilled without decomposition, but which can be freed from the last volatile constituents by so-called "incipient distillation", that is to say by prolonged heating to moderately elevated temperatures under reduced pressure, and can be purified in this manner. They are characterized by their refractive indexes.

If the new compounds are obtained in solid form after distilling off the solvent, they are purified by recrystallization. They are then characterized by their melting points.

PREPARATIVE EXAMPLES

Example 1

(a) The 4,6-dihydro-2H-thieno[3,4-c]-3-hydroxy-pyrazoles to be used as starting substances could be prepared, for example, as follows:

0.1 mol of a solution of sodium methylate in methanol was added to a solution of 4.6 g (0.1 mol) of methylhydrazine and 16 g (0.1 mol) of 4-oxo-tetrahydrothiophene-3-carboxylic acid methyl ester (for the preparation, see R. B. Woodward and R. H. Eastman, J. Amer. Chem. Soc., 68, (1946), page 2232) in 100 ml of methanol and the mixture was boiled under reflux for 2 hours. 100 ml of water were then added and the methanol was distilled off in vacuo. The solution which remained was adjusted to pH 5 by adding concentrated hydrochloric acid. The product which had precipitated was then filtered off and rinsed with a little ice-water. 8 g (51% of theory) of 2-methyl-4,6-dihydro-2H-thieno[3,4-c]-3-hydroxy-pyrazole were obtained in this manner in the form of a colorless powder with a melting point of 210° C.

The following compounds of the general formula

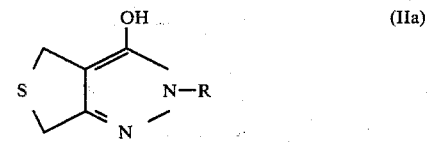

could be prepared in an analogous manner:

TABLE 1

| Compound | R | Yield (% of theory) | Melting point (°C.) |
|---|---|---|---|
| b | C₃H₇—iso | 79 | 191 |
| c | C₂H₅ | | |
| d | C₄H₉—sec. | | 204 |
| e |  | | 211 |
| f | CH₂—CH₂—CN | | |
| g |  | | |
| h | 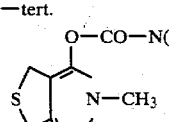 | | |
| i | CH(C₂H₅)₂ | | |
| k | C₄H₉—tert. | | |

(b) 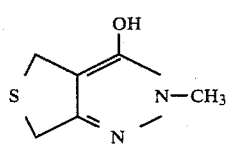 (1)

A mixture of 7.8 g (0.05 mol) of 2-methyl-4,6-dihydro-2H-thieno[3,4-c]-3-hydroxy-pyrazole, 8.4 g (0.06 mol) of potassium carbonate, 200 ml of acetonitrile and 5.4 g (0.05 mol) of N,N-dimethyl-carbamic acid chloride was stirred at 50° C. for 12 hours. After adding 200 ml of water, the mixture was extracted with 300 ml of toluene. The organic phase was dried over sodium sulphate and evaporated in vacuo. 10 g (88% of theory) of N,N-dimethyl-carbamic acid O-(2-methyl-4,6-dihydro-2H-thieno[3,4-c]pyrazol-3-yl) ester remained in the form of a beige powder with a melting point of 71° C.

Example 2

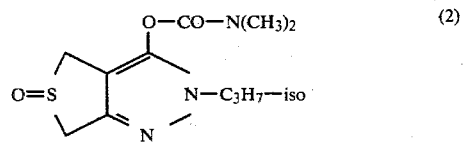 (2)

3.4 g (0.05 mol) of 50% strength hydrogen peroxide were added to a solution of 12.7 g (0.05 mol) of N,N-dimethyl-carbamic acid O-(2-isopropyl-4,6-dihydro-2H-thieno[3,4-c]pyrazol-3-yl) ester in 50 ml of glacial acetic acid at 5°–10° C. The mixture was subsequently stirred at room temperature for 6 hours and the solvent was then distilled off in vacuo. The residue was dissolved in 100 ml of methylene chloride and the solution was washed with a solution of 10 g of potassium carbonate in 15 ml of water. The organic phase was separated off and dried over sodium sulphate. The solvent was then distilled off in vacuo. 12.5 g (92% of theory) of N,N-dimethyl-carbamic acid O-(2-isopropyl-4,6-dihydro-2H-thieno[3,4-c]pyrazol-3-yl) ester 5-oxide were thus obtained in the form of light brown crystals with a melting point of 92° C.

Example 3

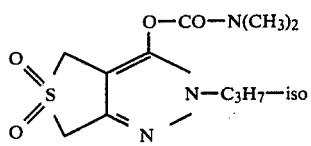 (3)

A solution of 21.3 g of m-chloroperbenzoic acid in 150 ml of chloroform was added dropwise to a solution of 12.7 g (0.05 mol) of N,N-dimethyl-carbamic acid O-(2-iso-propyl-4,6-dihydro-2H-thieno[3,4-c]pyrazol-3-yl) ester in 50 ml of chloroform at 5° C. The mixture was subsequently stirred overnight at room temperature and was then filtered. The filtrate was washed with 10 ml of concentrated potassium carbonate solution and dried over sodium sulphate. The solvent was then stripped off in vacuo. 13.8 g (96% of theory) of N,N-dimethyl-carbamic acid O-(2-iso-propyl-4,6-dihydro-2H-thieno[3,4-c]pyrazol-3-yl) ester 5,5-dioxide remained in the form of a beige powder with a melting point of 123° C.

The following compounds of the formula

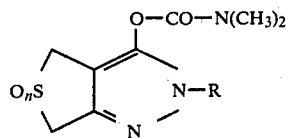 (I)

could be prepared analogously to one of Examples 1 to 3:

TABLE 2

| Compound No. | R | n | Yield (% of theory) | Physical data (refractive index; melting point °C.) |
|---|---|---|---|---|
| 4 | C₃H₇—iso | 0 | 85 | n_D^{24}:1.5310 |
| 5 | C₂H₅ | 0 | | |
| 6 | C₄H₉—sec. | 0 | | |
| 7 |  | 0 | | |
| 8 | C₂H₅ | 1 | | |
| 9 | C₂H₅ | 2 | | |
| 10 | C₄H₉—sec. | 1 | | |
| 11 | C₄H₉—sec. | 2 | | |
| 12 |  | 1 | | |
| 13 |  | 2 | | |
| 14 | CH₃ | 1 | | |
| 15 | CH₃ | 2 | | |
| 16 | CH₂—CH₂—CN | 0 | | |
| 17 | CH₂—CH₂—CN | 1 | | |
| 18 | CH₂—CH₂—CN | 2 | | |
| 19 |  | 0 | | |
| 20 | ⬡ | 0 | | |
| 21 | CH(C₂H₅)₂ | 0 | | |
| 22 | C₄H₉—tert. | 0 | | |

The active compounds are well tolerated by plants, have a favorable level of toxicity to warm-blooded animals, and can be used for combating arthropod pests, especially insects, and nematode pests which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus*, *Armadillidium vulgare* and *Porcellio scaber*;

from the class of the Diplopoda, for example *Blaniulus guttulatus*;

from the class of the Chilopoda, for example *Geophilus carpophagus* and *Scutigera* spec.;

from the class of the Symphyla, for example *Scutigerella immaculata*;

from the order of the Thysanura, for example *Lepisma saccharina*;

from the order of the Collembola, for example *Onychiurus armatus*;

from the order of the Orthoptera, for example *Blatta orientalis*, *Periplaneta americana*, *Leucophaea maderae*, *Blattella germanica*, *Acheta domesticus*, *Gryllotalpa* spp., *Locusta migratoria migratorioides*, *Melanoplus differentialis* and *Schistocerca gregaria*;

from the order of the Dermaptera, for example *Forficula auricularia*;

from the order of the Isoptera, for example *Reticulitermes* spp.;

from the order of the Anoplura, for example *Phylloxera vastatrix*, *Pemphigus* spp., *Pediculus humanus corporis*, *Haematopinus* spp. and *Linognathus* spp.;

from the order of the Mallophaga, for example *Trichodectes* spp. and *Damalinea* spp.;

from the order of the Thysanoptera, for example *Hercinothrips femoralis* and *Thrips tabaci*;

from the order of the Heteroptera, for example *Eurygaster* spp., *Dysdercus intermedius*, *Piesma quadrata*, *Cimex lectularius*, *Rhodnius prolixus* and *Triatoma* spp.;

from the order of the Homoptera, for example *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, *Myzus* spp., *Phorodon humuli*, *Ropalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, Pseudococcus spp. and *Psylla* spp.;

from the order of the Lepidoptera, for example *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *La-*

*phygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphoria erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.001 to 1% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods or nematodes, and especially insects) which comprises applying to the pests, or to a habitat thereof, a compound of the present invention alone or in the form of a composition containing as active ingredient a compound of the present invention in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The pesticidal activity of the compounds of this invention is illustrated by the following examples wherein the compounds according to the present invention are each identified by the number (given in brackets) from Examples 1 to 3 and Table 2:

Example 4

Myzus test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, the following compounds showed a superior activity compared with the prior art: (4) and (2).

Example 5

Doralis test (systemic action)

Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were each watered with 20 ml of the preparation of the active compound of the desired concentration in such a way that the preparation of the active compound penetrated into the soil without wetting the shoot. The active compound was taken up by the roots and passed to the shoot.

After the specified periods of time, the destruction in % was determined. 100% meant that all the aphids had been killed; 0% meant that none of the aphids had been killed.

In this test, for example, the following compounds showed a superior activity compared to the prior art: (4), (2) and (3).

Example 6

Critical concentration test/root-systemic action

Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (4), (1), (2) and (3).

It will be appreciated that the instant specification and examples are set forth by way of illustration and not limitation, and that various modifications and changes may be made without departing from the spirit and scope of the present invention.

We claim:

1. An N,N-dimethyl-carbamic acid O-(4,6-dihydro-2H-thieno[3,4-c]pyrazol-3-yl) ester or 5-oxide or 5,5-dioxide thereof of the formula

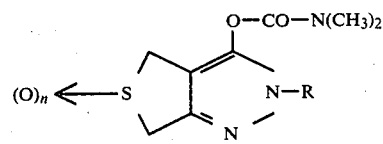

in which
R is $C_{1-5}$-alkyl optionally substituted by cyano, or $C_{3-6}$-cycloalkyl, and
n is 0, 1 or 2.

2. A compound according to claim 1, wherein such compound is N,N-dimethyl-carbamic acid O-(2-methyl- 4,6-dihydro-2H-thieno[3,4-c]-pyrazol-3-yl)ester of the formula

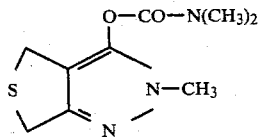

3. A compound according to claim 1, wherein such compound is N,N-dimethyl-carbamic acid O-(2-isopropyl-4,6-dihydro-2H-thieno[3,4-c]-pyrazol-3-yl)ester 5-oxide of the formula

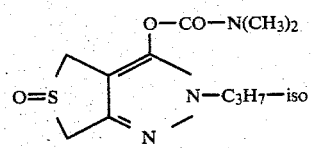

4. A compound according to claim 1, wherein such compound is N,N-dimethyl-carbamic acid O-(2-isopropyl-4,6-dihydro-2H-thieno[3,4-c]-pyrazol-3-yl)ester 5,5-dioxide of the formula

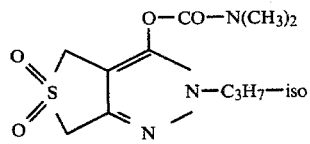

5. A compound according to claim 1, wherein such compound is N,N-dimethyl-carbamic acid O-(2-isopropyl-4,6-dihydro-2H-thieno[3,4-c]-pyrazol-3-yl)ester of the formula

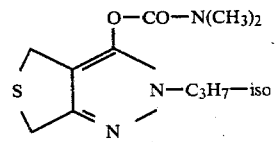

6. An insecticidal and nematocidal composition comprising as active ingredient an insecticidally or nematocidally effective amount of a compound according to claim 1 in admixture with a diluent.

7. A method of combating insects and nematodes which comprises applying to the pests, or to a habitat thereof, an insecticidally or nematocidally effective amount of a compound according to claim 1.

8. The method according to claim 7, wherein such compound is
N,N-dimethyl-carbamic acid O-(2-methyl-4,6-dihydro-2H-thieno[3,4-c]-pyrazol-3-yl)ester,
N,N-dimethyl-carbamic acid O-(2-isopropyl-4,6-dihydro-2H-thieno[3,4-c]-pyrazol-3-yl)ester 5-oxide,
N,N-dimethyl-carbamic acid O-(2-isopropyl-4,6-dihydro-2H-thieno[3,4-c]-pyrazol-3-yl)ester 5,5-dioxide, or
N,N-dimethyl-carbamic acid O-(2-isopropyl-4,6-dihydro-2H-thieno[3,4-c]-pyrazol-3-yl)ester.

* * * * *